United States Patent
Pinna et al.

(10) Patent No.: US 7,276,256 B2
(45) Date of Patent: Oct. 2, 2007

(54) COSMETIC OR HEALING GEL FOR APPLICATION TO THE HUMAN SKIN

(75) Inventors: Fausto Pinna, Lesmo (IT); Marco Pinna, Induno Olona (IT)

(73) Assignee: Biofarmitalia S.p.A., Milan (IT)

( * ) Notice: Subject to any disclaimer, the term of this patent is extended or adjusted under 35 U.S.C. 154(b) by 239 days.

(21) Appl. No.: 10/778,102

(22) Filed: Feb. 17, 2004

(65) Prior Publication Data

US 2004/0166131 A1    Aug. 26, 2004

(30) Foreign Application Priority Data

Feb. 26, 2003    (IT) .......................... MI2003A0343

(51) Int. Cl.
*A61K 36/00*    (2006.01)
*A61K 9/00*    (2006.01)
*A61K 9/14*    (2006.01)

(52) U.S. Cl. ...................... 424/725; 424/401; 424/486; 424/488

(58) Field of Classification Search ................ 424/725, 424/401, 486, 488
See application file for complete search history.

(56) References Cited

U.S. PATENT DOCUMENTS

| 4,291,025 A | 9/1981 | Pellico |
| 4,333,461 A | 6/1982 | Muller |
| 5,147,344 A | 9/1992 | Sachau et al. |
| 5,641,495 A * | 6/1997 | Jokura et al. ............... 424/401 |
| 6,444,199 B1 | 9/2002 | Renn |
| 6,602,592 B2 * | 8/2003 | Morikane et al. ........ 428/304.4 |

FOREIGN PATENT DOCUMENTS

| EP | 0 392 845 | 10/1990 |
| GB | 2 286 531 | 8/1995 |
| JP | 410211227 A * | 8/1998 |
| JP | 410226637 A * | 8/1998 |

OTHER PUBLICATIONS

Derwent Publications, AN 1981-71217, XP-002282916, JP 55-127311, Oct. 2, 1980.

* cited by examiner

*Primary Examiner*—Christopher R Tate
*Assistant Examiner*—Randall Winston
(74) *Attorney, Agent, or Firm*—Oblon, Spivak, McClelland, Maier & Neustadt, P.C.

(57) ABSTRACT

A gel formed from an intimate mixture of polyvinyl alcohol, an alkaline or alkaline earth metal borate, water and an alginate and/or a carrageenan, having cryogenic characteristics, substances with cosmetic and/or pharmacological characteristics being easily dispersible in said gel, to be released slowly when the gel is applied to the human skin.

12 Claims, No Drawings

COSMETIC OR HEALING GEL FOR APPLICATION TO THE HUMAN SKIN

FIELD OF THE INVENTION

The present invention relates to a gel spreadable directly on the human skin or on a flexible support which can then be rested on the skin, said gel exhibiting a cooling effect on human skin and able to contain, uniformly dispersed within it, substances with cosmetic and/or pharmacological characteristics whose release occurs slowly after the said gel has been applied to the human skin.

BACKGROUND OF THE INVENTION

Physical or physiological states or alterations of the human organism very frequently determine conditions which must be counteracted using various remedies. For example, in the case of a simple cold, balsamic inhalations are used (in the form of nasal sprays, vapours, aerosols and the like) in order to free the airways of the nose; creams and ointments are used to counteract reddening of the lower part of the nose and the upper lip (due mainly to the rubbing of the handkerchief used to blow the nose); and cold water or ice packs are used to alleviate the sensation of heat.

Another example, in the case of ocular or periocular traumas or in the period immediately following eye surgery, the affected area is cooled with ice or water to prevent or reduce localized swelling (by developing a localized cryogenic action); active substances with anti-bacterial, anti-edema, decongestant and analgesic effect are applied to the affected area (to develop a therapeutic action); and the eye is covered with a pad, to impart an occlusive effect to the eye and to retain on the eye the soothing, balsamic, aromatic and anti-bacterial vapours which have evolved from substances applied to the ocular region before the pad was rested onto it.

In these and in a large number of other cases it is therefore necessary to carry out a succession of separate operations which not only require time and attention but can often be carried out incorrectly.

SUMMARY OF THE INVENTION

The main object of the present invention is to form a gel which can be easily spread directly on the human skin or on a flexible support or pad which can then be applied to the human skin, the gel being in each case able to exert a cooling effect on the skin to which it is applied and able at the same time to also exert a balsamic or soothing effect, while allowing the controlled release of drugs, aromas, essences or the like.

These objects are attained by a gel consisting of an intimate mixture of several components, comprising water between 56% and 77%, polyvinyl alcohol between 2.5% and 23%, an alginate and/or carrageenan between 4% and 25%, an alkaline or alkaline earth metal tetraborate between 0.01% and 5.2%, and paraben products between 0.001% and 5.2%, the percentages being by weight.

Such a gel preferably contains at least one substance chosen from the group consisting of thickeners, stabilizers, gelling agents such as: sodium orthophosphates, potassium orthophosphates, calcium orthophosphates, alginic acid, agar-agar, carob flour, guar seed flour, tragacanth gum, gum arabic, xanthan gum, sorbitol, sorbitol syrup, mannitol, glycerol, pectin, phosphates and polyphosphates, microcrystalline cellulose, methylcellulose, hydroxypropylcellulose, hydroxypropylmethylcellulose, methylethylcellulose, carboxymethylcellulose and/or its derivatives between 0.7% to 6%, sorbitol between 0.004% and 5% and monopropylene glycol between 0.004% and 5%, the percentages being by weight, and even more preferably comprises between 0.03% and 15% by weight of at least one active substance chosen from the group consisting of pharmaceutical compounds, cosmetic substances, aromatic salts, plant essences and extracts, essential oils, balsamic substances and tinctures.

More specifically, gels were found particularly effective in which water is present in a quantity of about 71%, polyvinyl alcohol of about 13.5%, alginate and/or carrageenan of about 15%, and alkaline or alkaline earth metal tetraborate of about 0.2%, and thickeners, stabilizers, gelling agents and/or their derivatives are present in a quantity of about 1%, sorbitol of about 0.1% and monopropylene glycol of about 0.1%, while the active substances are present in a quantity of about 6%.

The paraben products (such as ethylparaben and methylparaben) are known substances of common usage in the cosmetic field, having preserving activity and able to prevent the degenerative phenomena: for example they consist of substances with bactericidal, fungicidal and antioxidant activity.

The gel according to the invention has a gummy consistency, is stable and able to retain considerable quantities of aromatic, therapeutic and cosmetic substances. The polyvinyl alcohol forms a gel with the alkaline or alkaline earth metal tetraborate, while the sodium and/or calcium alginate and/or the carrageenan affect the compactness or adhesiveness of the gel, retaining the water present within it. The thickeners, stabilizers, gelling agents, sorbitol and the monopropylene glycol have primarily the function of improving the stability and softness characteristics of the gel.

Due to the warmth of the human skin to which the gel is applied, the water begins to evaporate from the free surface of the gel, so causing cooling (cryogenic effect) of that part of the skin on which the gel is applied. Evaporation of the water causes molecules of aromatic substances (for example essential oils) which are possibly present in the gel to be drawn outwards, with consequent controlled release of aromatic and/or balsamic vapours which can be retained in contact with the skin for a long time if the gel is spread on a support, pad or patch applied to the skin itself. By the osmotic effect, part of the water present in the gel flows into the epidermal interstices (with a consequent hydrating effect on the skin itself) favouring the penetration and absorption into the skin of any cosmetic or pharmaceutical substances possibly dispersed within the gel.

Should the gel be spread onto a flexible and porous support (pad or patch or the like), such porosity determines the rate (i.e. the duration in time) of water evaporation and thus enables the rate or duration of transfer of cosmetic and pharmacological substances contained within the gel from the gel to the skin to be controlled.

DETAILED DESCRIPTION OF THE INVENTION

Some non-limiting embodiments will now be described to further clarify the understanding of the nature, composition and method of obtaining the gel.

EXAMPLE 1

30 kg of demineralised water, 0.120 kg of parabens (preserving agents) and 5.6 kg of polyvinyl alcohol are fed into a continuous mixer, heated to 70° C.; mixing is continued until a uniform mass is obtained (Phase A) in which the polyvinyl alcohol is completely dissolved in the water, the mass then being cooled to ambient temperature.

Separately, 1.2 kg of demineralised water and 0.300 kg of sodium tetraborate are separately fed into a steel mixer heated to a temperature between 25° and 30° C., and stirred until dissolution is complete to give a uniform mass (Phase B).

0.180 kg of monopropylene glycol, 0.140 kg of 70% sorbitol, 5 kg of a mixture of extracts of Aloe Vera, Calendula and Hypericum Perforatum, 3 kg of Eucalyptus, mint and white thyme essential oils and 20 kg of sodium alginate are added at ambient temperature (Phase C) to the same kneader (mixer) in which Phase A was prepared: the mass obtained in this manner is maintained under agitation for about 15-20 minutes while reversing the mixer rotation direction several times. The aforesaid Phase B is slowly added as a thin stream to this mass and mixing is continued for about 20-30 minutes to thus form a gel in which the components of plant origin are intimately dispersed. The fluidity of the gel can be increased by increasing the amount of Phase A added to the mixer; vice-versa, the fluidity can be decreased by adding further quantities of Phase B.

The gel thus obtained has cryogenic, cosmetic (balsamic) and cicatrising characteristics. It can be spread directly on the surface of the skin to be treated, or can be spread on a support (pad or patch), made for example from a 50 g/m² non-woven fabric formed from pure viscose fibres. Said patch can be applied between the upper lip and the nostrils of a person to allow the cryogenic cooling action of the evaporating water, the balsamic action of the vapours and the skin repairing action of the various substances incorporated in the gel.

EXAMPLE 2

28 kg of demineralised water, 0.120 kg of parabens (preservatives), 4.4 kg of polyvinyl alcohol and 0.5 kg of carboxymethylcellulose are fed into a mixer heated to 70° C. to obtain a uniform mass (Phase A) which is cooled to ambient temperature and then poured into a kneader into which a Phase C formed from 0.180 kg of monopropylene glycol, 2.0 kg of carboxymethyl betaglucan (having cicatrising action), 2.5 kg of eucalyptus, clove and black pepper essential oils, and 18 kg of sodium alginate is added while cold (over a period of about 15 to 20 minutes). The mixture is agitated for 15-20 minutes in both directions and then a Phase B, prepared separately by mixing 1.8 kg of demineralized water with 0.5 kg of sodium tetraborate in a steel vessel at a temperature of 20°-30° C. until complete dissolution, is slowly added as a thin stream over a period of 20-30 minutes, to give a gel whose viscosity can be increased by increasing the amount of Phase B or decreased by increasing the amount of Phase A.

This gel can be spread directly onto the region of the skin to be treated, or onto a porous support in the form of a pad or patch which can be applied onto the upper lip, beneath the nostrils of a person, to exhibit a cryogenic cooling action, the balsamic action of the vapours which evolve from the gel, and the skin repairing action due mainly to carboxymethyl betaglucan.

EXAMPLE 3

A liquid Phase A consisting of 32 kg of demineralised water, 0.120 kg of parabens (preserving agents), 4.8 kg of polyvinyl alcohol and 0.150 kg of chlorhexidine is prepared in a mixer heated to 70° C., the mass obtained is cooled and poured into a kneader into which 0.180 kg of monopropylene glycol, 0.140 kg of 70% sorbitol, 0.5 kg of betaglycyrrhetic acid, 0.8 kg of pineapple extract, 0.8 kg of Echinacea extract and 18 kg of sodium alginate are added, stirring in both directions for 15-20 minutes.

A solution of sodium tetraborate (0.200 kg) and demineralised water (0.8 kg) is prepared separately in a steel mixer heated to 25-30° C., to give a Phase B which is slowly added as a thin stream to the aforesaid kneader in which the mass is maintained in movement for a time of 20-30 minutes, to give rise to the formation of a gel whose fluidity can be increased by increasing the quantity of the Phase B, or reduced by increasing the quantity of the Phase A.

This gel can be advantageously spread onto a pad formed from a 50 g/m² non-woven fabric of pure viscose which can be applied over one eye (following surgery) to lightly compress the eyelids, allowing any exudate to emerge and developing a localized cooling effect (cryogenic effect), anti-edemic effect and antibacterial effect.

EXAMPLE 4

33 kg of demineralised water, 0.150 kg of parabens (antioxidants and preservatives), 5.3 kg of polyvinyl alcohol, and 0.8 kg of carboxymethylcellulose are fed into a mixer heated to 70° C. and stirred until dissolution is complete. The mixture is cooled and is poured into a kneader into which 0.140 kg of 70% of sorbitol, 0.8 kg of betaglycyrrhetic acid, 0.3 kg of pineapple extract, 0.3 kg of Echinacea extract and 12 kg of sodium alginate are added. The mixture is stirred in both directions at ambient temperature for about 20-30 minutes, then a Phase B, prepared separately by mixing 1.2 kg of demineralised water and 0.150 kg of sodium tetraborate at 25 to 30° C. in a steel vessel until dissolution is complete, is slowly added as a thin stream. A gel is obtained whose fluidity can be increased by increasing the quantity of Phase A or decreased by increasing the quantity of Phase B.

The gel can for example be spread onto a pad of non-woven fabric which can then be applied onto an eye, to develop a localized cooling, anti-edemic and healing effect.

What is claimed is:

1. A gel for application to the human skin, consisting of an intimate mixture of several components comprising:
   water between 56% and 77%,
   polyvinyl alcohol between 2.5% and 23%,
   an alginate and/or carrageenan between 4% and 25%,
   an alkaline metal tetraborate or alkaline earth metal tetraborate between 0.01% and 5.2%,
   and one or more additives selected from the group consisting of preserving additives, antioxidant additives, antioxidant synergists, colorant additives, and aromatic additives, between 0.0001% and 5.2%, the percentage being by weight;
   wherein said gel promotes a cooling effect on the skin to which it is applied.

2. A gel as claimed in claim 1, further comprising at least one substance selected from the group consisting of thickeners, stabilizers, and/or gelling agents between 0.7% to 6%, the percentages being by weight.

3. A gel as claimed in claim 1, further comprising between 0.03% and 15% by weight of at least one active substance selected from the group consisting of pharmaceutical compounds, cosmetic substances, aromatic salts, plant essences and extracts, essential oils, balsamic substances and tinctures.

4. A gel as claimed in claim 2, further comprising between 0.03% and 15% by weight of at least one active substance selected from the group consisting of pharmaceutical compounds, cosmetic substances, aromatic salts, plant essences and extracts, essential oils, balsamic substances and tinctures.

5. A gel as claimed in claim 1, wherein water is present in a quantity of about 71%, polyvinyl alcohol of about 13.5%, alginate and/or carrageenan of about 15%, and alkaline metal tetraborate or alkaline earth metal tetraborate of about 0.2%, the percentages being by weight.

6. A gel as claimed in claim 2, further comprising sorbitol in a quantity of about 0.1% and monopropylene glycol of about 0.1%, the percentages being by weight.

7. A gel as claimed in claim 3, wherein said active substances are present in a quantity of about 6% by weight.

8. A gel as claimed in claim 4, wherein said active substances are present in a quantity of about 6% by weight.

9. A flexible porous support, on one surface of which a layer of gel in accordance with claim 1 is spread.

10. A gel as claimed in claim 2, wherein thickeners, stabilizers, and/or gelling agents are present and are in a quantity of about 1% by weight.

11. A gel as claimed in claim 2, further comprising sorbitol between 0.004 wt. % and 5 wt. % and/or monopropylene glycol between 0.004 wt. % and 5 wt. %.

12. A gel as claimed in claim 1, further comprising sorbitol between 0.004 wt. % and 5 wt. % and/or monopropylene glycol between 0.004 wt. % and 5 wt. %.

* * * * *